(12) United States Patent
Abate

(10) Patent No.: US 7,143,763 B2
(45) Date of Patent: Dec. 5, 2006

(54) DEVICE FOR WASHING NASAL CAVITIES AND COLLECTING CATARRHAL MATTER

(75) Inventor: Riccardo Abate, Battaglia (IT)

(73) Assignee: Flaem Nuova S.p.A. (IT)

( * ) Notice: Subject to any disclaimer, the term of this patent is extended or adjusted under 35 U.S.C. 154(b) by 895 days.

(21) Appl. No.: 10/288,787

(22) Filed: Nov. 6, 2002

(65) Prior Publication Data
US 2003/0089367 A1    May 15, 2003

(51) Int. Cl.
*A61M 11/00* (2006.01)
*B05B 7/30* (2006.01)

(52) U.S. Cl. .................. 128/200.14; 239/348

(58) Field of Classification Search ........... 128/200.14, 128/200.18, 200.19, 200.21; 251/83; 239/337, 239/338, 347, 348, 349, 569
See application file for complete search history.

(56) References Cited

U.S. PATENT DOCUMENTS

| | | | | |
|---|---|---|---|---|
| 68,038 | A * | 8/1867 | Brown ........................ | 73/333 |
| 210,766 | A * | 12/1878 | Duffy ......................... | 137/512 |
| 247,724 | A * | 9/1881 | Whelan ....................... | 251/83 |
| 248,579 | A * | 10/1881 | Curtis ........................ | 239/417.5 |
| 560,225 | A * | 5/1896 | Mills ......................... | 239/348 |
| 788,757 | A * | 5/1905 | Deeks ......................... | 239/338 |
| 853,455 | A * | 5/1907 | Holmgren ..................... | 239/347 |
| 1,022,601 | A * | 4/1912 | Rumberg et al. .............. | 604/30 |
| 1,042,556 | A * | 10/1912 | Holland ....................... | 239/338 |
| 1,146,723 | A * | 7/1915 | Losh .......................... | 251/83 |
| 1,220,942 | A * | 3/1917 | Bradley ....................... | 239/424 |
| 1,331,643 | A * | 1/1920 | Holland ....................... | 239/369 |
| 1,357,452 | A * | 11/1920 | Hall .......................... | 239/348 |
| 1,713,902 | A * | 5/1929 | Hartman ....................... | 239/348 |
| 1,737,895 | A * | 12/1929 | Sachsenmaier ................. | 239/341 |
| 1,738,757 | A * | 12/1929 | Bragdon ....................... | 239/347 |
| 1,738,863 | A * | 12/1929 | Bragdon ....................... | 239/347 |
| 1,743,292 | A * | 1/1930 | Tittemore ..................... | 239/348 |
| 1,843,900 | A * | 2/1932 | Martinet ...................... | 239/341 |
| 1,856,811 | A * | 5/1932 | Inaki ......................... | 604/38 |
| 1,864,188 | A * | 6/1932 | Deutsch ....................... | 239/8 |
| 2,171,501 | A * | 8/1939 | Gebauer ....................... | 239/337 |
| 2,243,435 | A * | 5/1941 | Macgill ....................... | 239/347 |
| 2,390,313 | A * | 12/1945 | Dalrymple ..................... | 222/74 |
| 2,539,559 | A * | 1/1951 | Ward et al. ................... | 239/337 |
| 2,546,214 | A * | 3/1951 | Curry ......................... | 128/200.21 |
| 2,605,764 | A * | 8/1952 | Adams et al. .................. | 128/200.18 |
| 2,623,785 | A * | 12/1952 | Henchert ...................... | 239/337 |
| 2,634,748 | A * | 4/1953 | Morrison ...................... | 137/523 |
| 2,678,044 | A * | 5/1954 | Szekely et al. ................ | 128/200.18 |
| 2,749,179 | A * | 6/1956 | Almquist ...................... | 239/215 |

(Continued)

FOREIGN PATENT DOCUMENTS

EP    1 108 422 A2 *  6/2001

Primary Examiner—Aaron J. Lewis
(74) Attorney, Agent, or Firm—McGlew & Tuttle, PC

(57) ABSTRACT

The invention relates to a device for washing the nasal cavities with a nebulized treatment liquid. It comprises a base body, a atomizer chamber containing a washing liquid, means for nebulizing the liquid in said chamber and dispensing the atomized liquid to the nasal cavities for washing and a chamber for collecting the return liquid and catarrhal matter from the nasal cavities. The atomizer chamber (12) and collection chamber (13) are positioned side by side above the base body, and the collection chamber communicates with a dispensing exit of the atomized liquid to the nasal cavities. The two chambers may be defined each by a respective element or by a single piece.

14 Claims, 3 Drawing Sheets

U.S. PATENT DOCUMENTS

| | | | | |
|---|---|---|---|---|
| 2,827,329 A * | 3/1958 | Bullock | | 239/344 |
| 2,861,569 A * | 11/1958 | Emerson | | 128/202.22 |
| 2,926,456 A * | 3/1960 | Biro | | 239/654 |
| 3,093,155 A * | 6/1963 | Dawes | | 137/269 |
| 3,154,224 A * | 10/1964 | Wakeman | | 222/402.12 |
| 3,206,175 A * | 9/1965 | Boteler | | 261/16 |
| 3,254,807 A * | 6/1966 | Boch et al. | | 222/394 |
| 3,258,176 A * | 6/1966 | Raczynski | | 222/397 |
| 3,292,895 A * | 12/1966 | Leger et al. | | 251/83 |
| 3,301,255 A * | 1/1967 | Thompson | | 128/200.18 |
| 3,352,305 A * | 11/1967 | Freedman | | 128/200.19 |
| 3,381,900 A * | 5/1968 | Miller | | 239/323 |
| 3,398,743 A * | 8/1968 | Shalit | | 604/36 |
| 3,534,739 A * | 10/1970 | Bryne | | 606/22 |
| 3,537,448 A * | 11/1970 | Liston | | 128/200.21 |
| 3,603,308 A * | 9/1971 | Spradling et al. | | 128/200.21 |
| 3,647,143 A * | 3/1972 | Gauthier et al. | | 239/342 |
| 3,653,379 A * | 4/1972 | Glenn | | 128/204.21 |
| 3,658,059 A * | 4/1972 | Steil | | 128/200.21 |
| 3,664,337 A * | 5/1972 | Lindsey et al. | | 128/200.18 |
| 3,702,114 A * | 11/1972 | Zacarian | | 128/200.23 |
| 3,865,106 A * | 2/1975 | Palush | | 128/200.18 |
| 4,150,071 A * | 4/1979 | Pecina | | 261/78.2 |
| 4,429,835 A * | 2/1984 | Brugger et al. | | 239/338 |
| 4,604,999 A * | 8/1986 | Maeda | | 128/200.21 |
| 4,657,007 A * | 4/1987 | Carlin et al. | | 128/200.18 |
| 4,685,622 A * | 8/1987 | Shimohira et al. | | 239/346 |
| 4,801,292 A * | 1/1989 | Watson | | 604/36 |
| 5,666,945 A * | 9/1997 | Davenport | | 128/200.14 |
| RE36,070 E * | 2/1999 | Ballini et al. | | 128/200.14 |
| 6,007,003 A * | 12/1999 | Wang | | 239/525 |
| 6,021,776 A * | 2/2000 | Allred et al. | | 128/200.21 |
| 6,085,741 A * | 7/2000 | Becker | | 128/200.21 |
| 6,085,997 A * | 7/2000 | Mills et al. | | 239/337 |
| 6,135,358 A | 10/2000 | Ballini | | |
| 6,238,377 B1 * | 5/2001 | Liu | | 604/289 |
| 6,595,203 B1 * | 7/2003 | Bird | | 128/200.21 |
| 6,612,303 B1 * | 9/2003 | Grychowski et al. | | 128/200.21 |
| 6,736,792 B1 * | 5/2004 | Liu | | 604/94.01 |
| 6,907,879 B1 * | 6/2005 | Drinan et al. | | 128/202.22 |

* cited by examiner

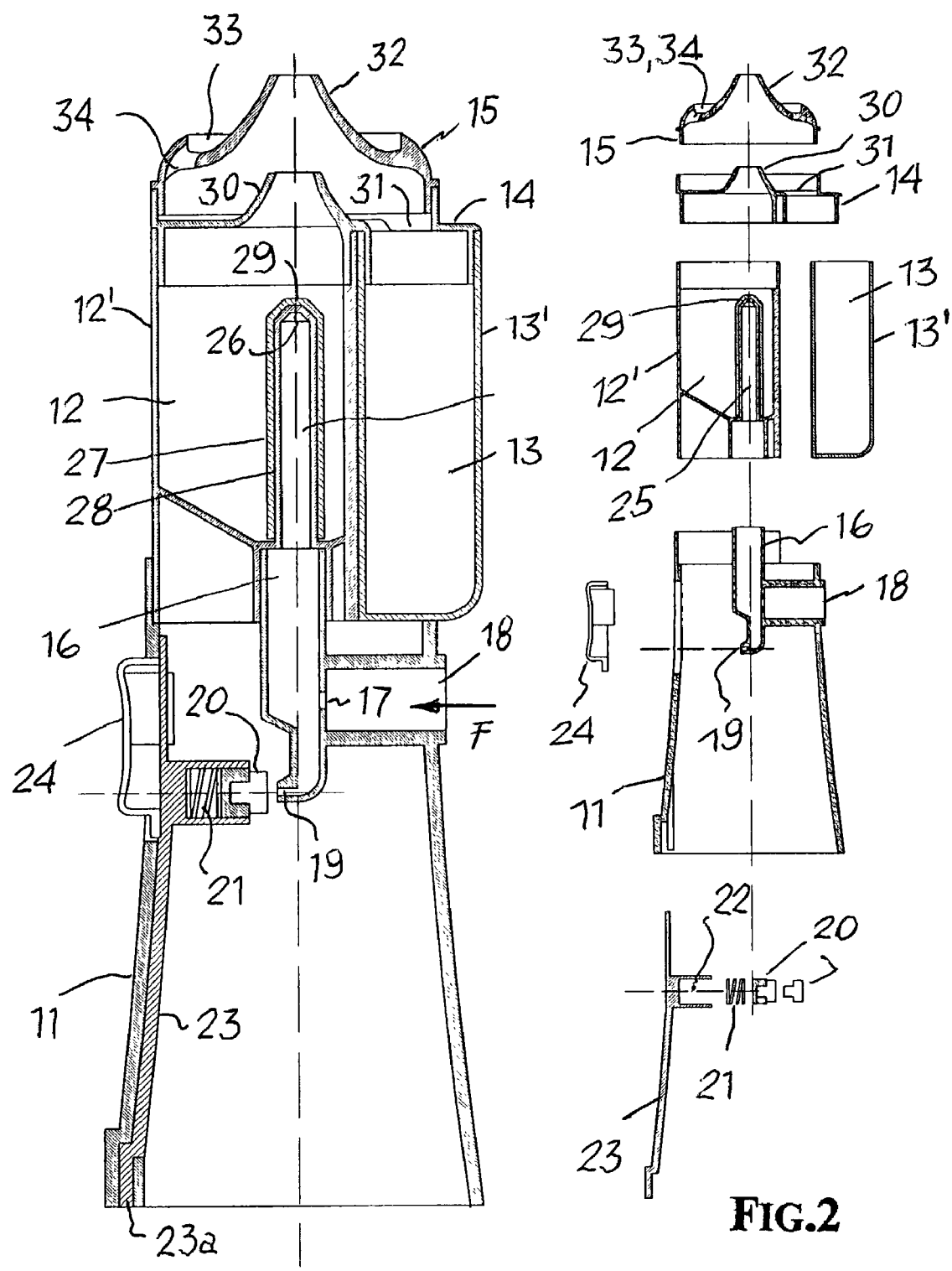

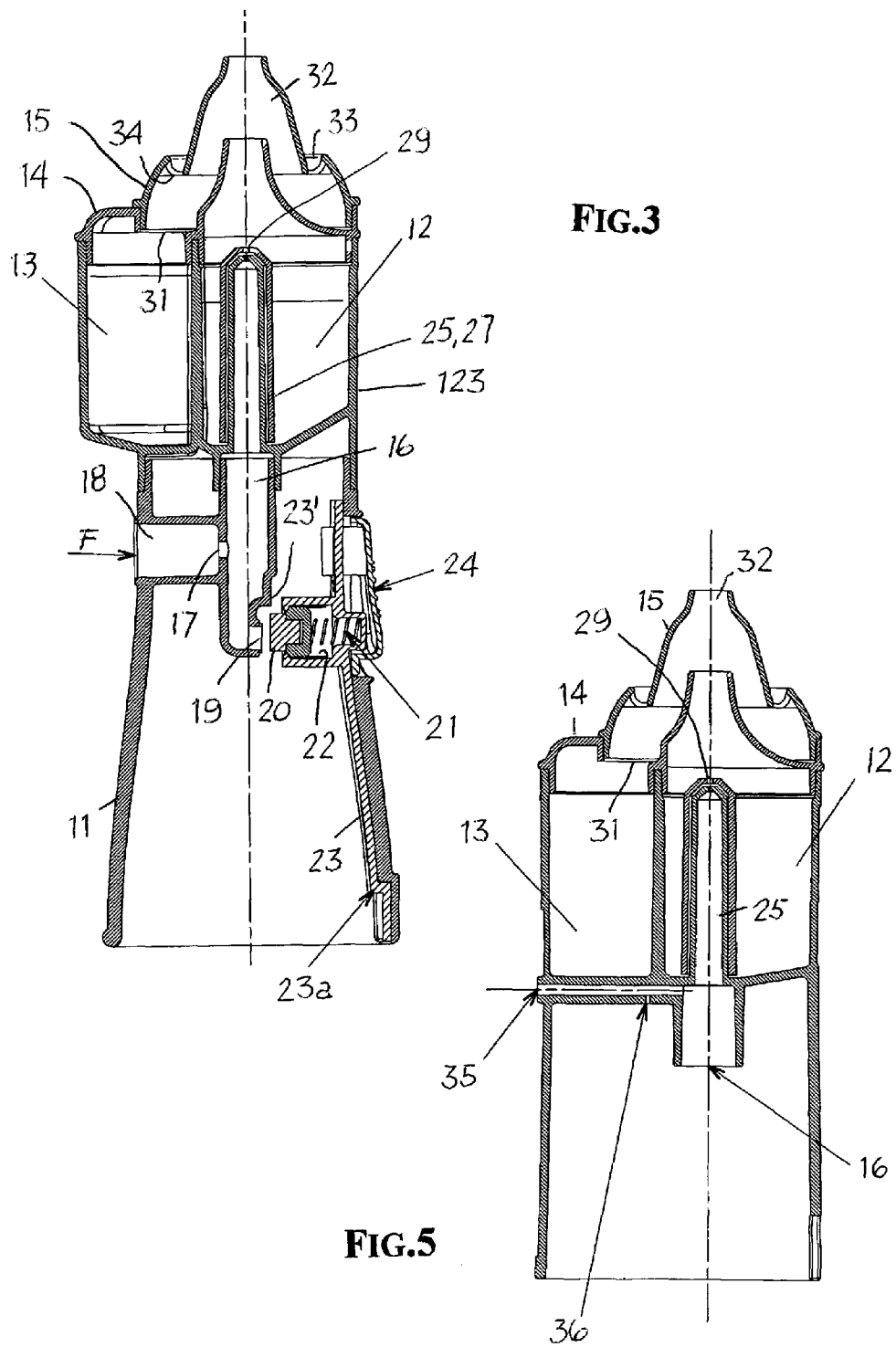

DEVICE FOR WASHING NASAL CAVITIES AND COLLECTING CATARRHAL MATTER

FILED OF THE INVENTION

This invention generally concerns treatment liquid nebulizing devices and refers especially to a device for washing the nasal cavities, also called nasal douche.

STATE OF THE ART

Devices are already known, for example for aerosol therapy and the washing, or douche, of the nasal cavities, etc., that comprise a tank for a medical or washing liquid and means for taking the medical or washing liquid from the tank and nebulizing this by means of a flow of air under pressure coming from a compressor and for conveying the nebulized liquid to the nasal cavities through a dispensing hole, a mask, a mouthpiece or other accessory.

One of such devices essentially comprises a bell-shaped body that defines an atomizer chamber containing a washing liquid into which is submerged a spray nozzle connected to an injector of air under pressure aligned with an exit hole for the atomized liquid to escape towards the user. A second body arranged like a skirt around the bell-shaped body defines, with the same bell-shaped body, a chamber for collecting, through an opening in the top, catarrhal matter from the treated nasal cavities. The second body or skirt is movable in height between two positions to define two different ways of using the device.

Substantially, the chamber containing the liquid to be atomized and the secretion collection chamber are concentric, defined by component parts associated in a relatively complex manner and which make the device structure complicated and costly.

Another device known for washing nasal cavities has been conceived and configured to make the device easier to use, to clean and to store. For this purpose, the washing liquid tank and chamber for collecting the return liquid and secretions is designed on two levels, the first in a bottom part and the second in an upper part of the device body, separated.

On the other hand, the compressor to which an aerosol or nasal douche device is connected is not always selected and sized to provide a flow of air suitably compatible in terms of flow rate and pressure with the characteristics of the device and/or the size of the atomized particles to be generated and used. Sometimes, the compressor is oversized, so flow rate and pressure are excessive with respect to the envisaged requirements and flow of atomized liquid to be obtained. In other cases the atomizing device can be connected to a source of air under pressure available in another device and not therefore specifically selected for the atomizing device in question. In other cases still, intermittent dispensing is required of the atomized liquid and consequently a supply of pulsating atomized air without disconnecting or blocking the source of air under pressure, meaning the compressor. Hence the need to be able to conveniently manage the flow and atomized air pressure in all the nebulizing devices of the aforementioned type and for the aforementioned use.

OBJECTS AND SUMMARY OF THE INVENTION

On the basis of what has been said, one object of the invention is to provide an atomizing device, especially for the aforementioned use, made according to a new, original configuration, arrangement and combination of parts to ensure simple assembly and able to make it easier to load the medical or washing liquid into the respective chamber and disassemble the parts in order to access these and clean them without any difficulty.

Another object of the invention is to provide a nebulizing device for washing nasal cavities, where the atomizing chamber and the chamber for collecting secretions are at the same level, defined by a single integral piece or by two component parts arranged side by side, with the result of giving the device a particular and distinctive outward appearance.

Another object of the invention is to provide an atomizing device for the aforementioned use complete with innovative valves for regulating the flow of atomizing air, so as to maintain this flow practically constant whatever the pressure of the incoming air thanks to the automatic release of the excess air towards the outside.

This appears very advantageous and makes it possible to keep the operating pressure of the device within the maximum limit level even when the compressor that supplies the air under pressure to which it is connected is more powerful than necessary, meaning having an operating pressure above device operating pressure. In other words, the atomizing device can also be connected to oversized compressors without affecting correct washing liquid atomisation and an appropriate use of the atomized liquid.

Said objects are achieved, in accordance with the invention, with a nebulizing device for washing the nasal cavities according to claim 1 and having an atomized air flow control valve in conformity with claim 11.

BRIEF DESCRIPTION OF DRAWINGS

The nebulizing device of the invention here will be described in further detail by making reference to the attached drawings, illustrative but not limitative, in which:

FIG. 1 is a vertical section of the device according to a first embodiment;

FIG. 2 is a sectional and separate view of the component parts of the device in FIG. 1;

FIG. 3 is a vertical section of the device according to a different realisation of the chambers positioned side by side;

FIG. 5 is a section of a device incorporating a variation of the means of regulating the atomisation air flow.

DETAILED DESCRIPTION OF THE INVENTION

Figure 4:
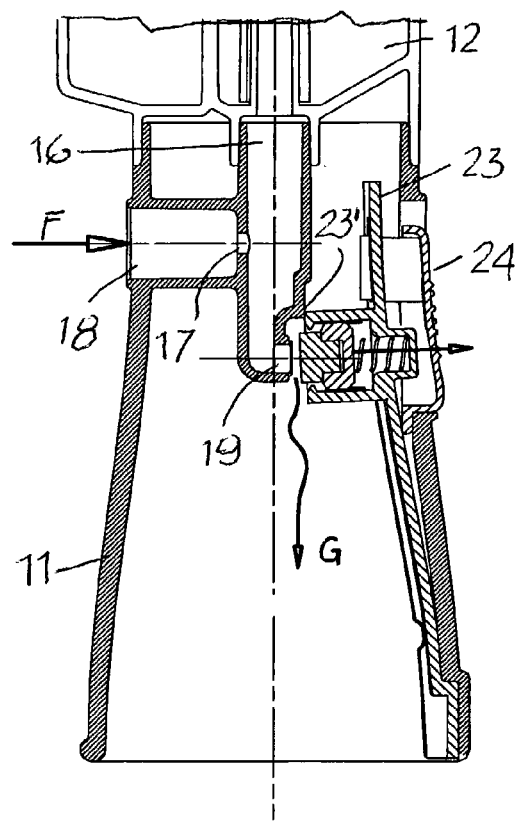
FIG. 4 represents part of the device seen in the condition of an automatic vent of the excess air.

As represented, the device of the invention comprises a possible base body 11 and, above this body, two chambers 12, 13 with superimposed an intermediate cover part 14 and a top cover 15. All the component parts are for example in a plastic material.

The base body 11, when present, acts both as a support and as a grip for using the device. In said body, a central duct 16 is provided, which open at the top and communicating, through a radial hole 17, with a branch 18 to which a small pipe —not shown— is connected for conveying air under pressure from a compressor in the direction of the arrow F (FIGS. 1 and 3). According to FIGS. 1–4, the duct 16 features, on the bottom, a vent orifice 19 facing a shutter 20 designed for controlling the air flow in the duct itself.

The shutter 20 is fitted, together with a relevant adjustment spring 21, in a housing 22 which in the example shown, is advantageously integrated with a flexible blade 23. This has an end 23a blocked and stopped in the body 11 and can be moved by bending, by means of a button 24, towards duct 16 to close the orifice 19, and away from the duct by elastic reaction, to open the orifice.

The two chambers 12, 13 above the body 11 are placed side by side, at the same level. They can each be defined by a respective element 12', 13' as shown in FIGS. 1 and 2. Then, the two elements 12', 13' that delimit said chambers are both positioned and stopped in the top part of the base body 11 and are joined by the intermediate part 14 when this is superimposed.

Otherwise, the two chambers 12, 13 can be achieved in a single piece 123, as shown in FIG. 3, that fits onto the top part of the base body 11.

A first chamber 12 is intended to receive and contain a medical or washing liquid, in effect constituting a tank and an atomizing chamber for said liquid. The second chamber 13 represents a receptacle for collecting the return washing liquid and catarrhal matter from the nasal cavities of the user.

From the bottom of the atomizing chamber 12, a channel 25 elevates which below is pressure fitted and sealed with the air duct 16 in the base body 11 and above terminates with an injector nozzle 26 turned upwards. A tubular cap 27 is fitted around channel 25 and delimits with the outer surface of this, an annular duct 28. The latter, at the bottom, is open radially towards the chamber 12, near its bottom, and dips into the liquid contained inside, while at the top it joins up with a atomizer nozzle 29 which is above and aligned with the injector nozzle 26.

This way, the flow of air from the duct 16, moves up the channel 25 and passing through the injector nozzle 26, sucks up because of the vacuum formed, the washing liquid from the bottom of chamber 12, forcing this through the atomizer nozzle 29 and forming an atomized liquid suitable for washing the nasal cavities.

The flow of atomized air in channel 25 can be regulated by means of the shutter 20, associated with the vent orifice 19 and moved by means of button 24. For this purpose, the movement by bending of blade 23 towards duct 16 is restricted, directly or indirectly (FIG. 4), by a stop 23', and the shutter 20 is movable axially in its housing 22 contrasted by the adjustment spring 21. This spring can be selected and/or calibrated so that even when the button is pressed fully down until the blade 23 is resting against stop 23', and to move the shutter 20 to vent orifice 19 obstruction position, the shutter itself can move back (FIG. 4) in case of excessive pressure in the duct 25, thereby opening the orifice 19 to release air outwards according to the arrow G and cause automatic reduction of the pressure to the value prescribed and desired for better device operation in terms of yield and size of nebulized liquid particles.

Figure 4A:
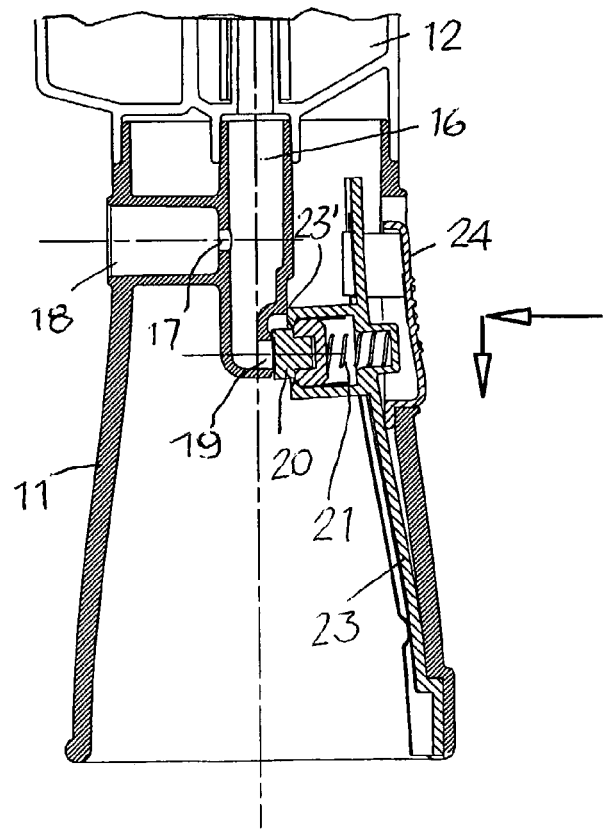
FIG. 4A shows the same view as FIG. 4, but with the button blocked in pressed position.

In addition, button 24 can be fitted for locking in the vent orifice closing pressed position and in any case to permit automatic air release due to reverse movement of the shutter in the event of excessive pressure. This being such, the button can be configured, or movable in relation to the blade supporting it, as shown in FIG. 4A, or otherwise associated with means that enable it to stop in said pressed position, without having to restrain it manually.

Constructively, the intermediate cover part 14 rests and is restrained on the top of the two elements 12', 13' or of the single piece 123 delimiting the two chambers 12,13, covering both of these and providing access to each of them when removed. In any case, said intermediate part 14 features, on the one side, a concentrator 30 of the atomized liquid that narrows towards the top and which is in line with the atomizer nozzle 29 of the nebulizing chamber 12 and, on the other side, a return opening 31 located above the collection chamber 13.

The top cover 15 rests on intermediate part 14. Its base surrounds and encloses the concentrator 30 and the return opening 31 in intermediate part 14, while the remainder features a truncated cone shaped exit section 32, positioned in line with the concentrator 30 and acting as a conveyor and dispenser of the atomized liquid towards the nasal cavity for envisaged washing action, but also for the recovery of the washing secretions towards the collection chamber 13.

Around the truncated cone exit section 32 is envisaged an annular channel 33 on the bottom of which are a number of holes 34 for further transit into the collection chamber 13 of the return liquid and the catarrhal matter also coming from the imperfect coupling between nose and device.

Finally, the atomizing device, in a simplified embodiment shown in FIG. 5, while always featuring the two adjacent chambers 12, 13, may be without the shutter and relevant control parts, and the flow of atomized air can be modulated manually with a finger by means of an intermittent orifice 35, joined to a duct 16 conveying air under pressure and which is facing onto one side of the base body. Furthermore, upstream of the intermittent orifice 35 will be a calibrated vent hole 36 for the controlled release of excess air and pressure adjustment.

The invention claimed is:

1. A device for washing the nasal cavities with a nebulized treatment liquid, comprising:
   a base body;
   an atomizer chamber containing a washing liquid;
   means for removing the liquid from said atomizer chamber and for nebulizing the liquid in said atomizer chamber and for dispensing the atomized liquid to the nasal cavities for washing;
   a collection chamber for collecting the return liquid and catarrhal matter from the nasal cavities, said atomizer chamber being positioned adjacent to said collection chamber above said base body, said collection chamber communicating with a dispensing exit of the atomized liquid to the nasal cavities; and
   a duct for conveying compressed air, said duct joining an intermittent orifice accessible from an outside to be opened and closed to modulate the flow of air, said duct having an outlet for releasing the air and adjusting excess pressure.

2. The device according to claim 1, wherein a channel elevates from the bottom of said atomizer chamber and communicates, on one side, with the duct conveying air under pressure at base body level and has, on the other side, an injector nozzle placed in line with an atomizer nozzle which receives the washing liquid taken from said atomizer chamber.

3. A device for washing the nasal cavities with a nebulized treatment liquid by means of a flow of air under pressure, said device comprising:
   a base body;
   an atomizer chamber containing the treatment liquid;
   means for taking from and atomizing the liquid in said chamber and for dispensing the atomized liquid for use;
   a chamber for collecting the return liquid and catarrhal matter, said atomizer chamber and said collection chamber being positioned side by side above said base body, said collection chamber communicating with a dispensing exit of the nebulized liquid to the nasal cavities, said atomizer chamber and said collection chamber being formed as a single piece or delineated by a respective element;

a duct for conveying air under pressure having a vent hole; and an elastic blade secured to said body having a shutter associated with said vent hole of said duct, said shutter being movable by means of a button to move the shutter from an open position to a closed position such that when said shutter is in a closed position said shutter is in contact with said vent hole joined to said duct.

4. The device according to claim 3, wherein said shutter associated with said vent hole of said duct controls the flow of air towards the injector nozzle.

5. The device according to claim 4 wherein said shutter is housed with an adjustment spring in a housing on board said elastic blade, said shutter being associated with the vent orifice such that said shutter compresses said spring in the case of excessive pressure in said duct.

6. The device according to claim 5, wherein said button is locked fast in closed position, said button being movable in relation to said blade and/or associated with means for stopping it in said closed position.

7. The device according to claim 3, wherein said atomizer chamber and said collection chamber are each delineated by a respective element, said atomizer chamber and said collection chamber being joined side by side, associated at the bottom with the base body and joined at the top by an intermediate cover part.

8. The device according to claim 7, wherein said intermediate cover part comprises on the one side a concentrator of atomized liquid and on the other side a return opening above the collection chamber, and on said intermediate cover part is arranged a cover having abase that surrounds the concentrator and return opening in the intermediate cover part and a truncated cone shaped section in line with the concentrator and acting as an external exit for the nebulized liquid and an inlet for the return liquid and catarrhal matter into said collection chamber.

9. The device according to claim 3, wherein said atomizer chamber and said collection chamber are both defined by a single piece associated at the bottom with the base body and on the top with an intermediate cover part.

10. The device according to claim 3, wherein a channel elevates from the bottom of said atomizer chamber and communicates, on one side, with said duct conveying air under pressure at base body level and has, on the other side, an injector nozzle placed in line with the washing liquid taken from said atomizer chamber.

11. A valve device for controlling atomized air flow and pressure in electrical medical appliances, said valve device comprising:

a base body;

an atomizer chamber containing a treatment liquid;

means for taking and atomizing liquid from said chamber and dispensing the atomized liquid towards the user;

a duct for conveying air under pressure to said taking and atomizing means, said duct including a vent orifice;

a shutter associated with said vent orifice of said duct, said shutter being secured to a flexible blade, said flexible blade being mounted to said body and movable by means of a button to move the shutter to from a first to a second position such that when said shutter is in the second position said shutter closes said vent hole to form a vacuum within said duct, whereby said treatment liquid mixes with the air conveyed to said taking and atomizing means.

12. The valve device according to claim 11, wherein said shutter is housed with an adjustment spring in a housing on board said elastic blade and is associated with said vent orifice such that said shutter compresses said spring in case of excessive pressure in said duct.

13. The valve device according to claim 11, wherein said button is locked fast in said second position, said button being movable in relation to the blade and/or associated with means for stopping it in said second position.

14. The valve device according to claim 12, wherein the elastic blade is associated with a stationary stop position to restrict movement of blade towards the vent orifice when pressed by means of the control button.

* * * * *

UNITED STATES PATENT AND TRADEMARK OFFICE
CERTIFICATE OF CORRECTION

PATENT NO.        : 7,143,763 B2                                            Page 1 of 1
APPLICATION NO.   : 10/288787
DATED             : December 5, 2006
INVENTOR(S)       : Abate It is certified that error appears in the above-identified patent and that said Letters Patent is hereby corrected as shown below:

On the title page insert item --[30] Foreign Application Priority Data:

BS2001U000090         ITALY          November 12, 2001
BS2001U000091         ITALY          November 12, 2001--

Signed and Sealed this

Twenty-second Day of May, 2007

JON W. DUDAS
*Director of the United States Patent and Trademark Office*